United States Patent [19]

Bright

[11] Patent Number: 5,242,911
[45] Date of Patent: Sep. 7, 1993

[54] BRIDGED BICYCLIC IMIDES AS ANXIOLYTICS AND ANTIDEPRESSANTS

[75] Inventor: Gene M. Bright, Groton, Conn.

[73] Assignee: Pfizer Inc., New York, N.Y.

[21] Appl. No.: 355,515

[22] Filed: May 23, 1989

Related U.S. Application Data

[63] Continuation-in-part of Ser. No. 312,772, Jun. 17, 1988, abandoned.

[51] Int. Cl.⁵ .................. A61K 31/55; C07D 223/32
[52] U.S. Cl. ............................ 514/183; 514/216; 514/256; 544/230; 544/295; 540/520; 540/453; 540/461
[58] Field of Search .............. 544/295, 230; 540/453, 540/461, 520; 514/183, 216, 256

[56] References Cited

U.S. PATENT DOCUMENTS

| | | | |
|---|---|---|---|
| 3,717,634 | 2/1973 | Wu et al. | 260/256.4 |
| 3,907,801 | 9/1975 | Wu et al. | 260/268 |
| 4,006,233 | 2/1977 | Shepard et al. | 424/251 |
| 4,173,646 | 11/1979 | Shepard et al. | 424/270 |
| 4,182,763 | 1/1980 | Casten et al. | 424/251 |
| 4,423,049 | 12/1983 | Temple, Jr. | 424/251 |
| 4,507,303 | 5/1985 | Ishizumi et al. | 514/255 |
| 4,543,355 | 9/1985 | Ishizumi et al. | 514/253 |
| 4,562,255 | 12/1985 | Freed et al. | 544/357 |
| 4,748,240 | 5/1988 | Stack et al. | 544/47 |

OTHER PUBLICATIONS

Chem. Abst. vol. 101, 1984, Abst. No. 23432K abstracting Korgeonkar et al. J. Indian Soc. (1983) vol. 60, No. 9, pp. 874–876.

*Primary Examiner*—Robert T. Bond
*Attorney, Agent, or Firm*—Peter C. Richardson; Gregg C. Benson; A. Dean Olson

[57] ABSTRACT

A series of bridged bicyclic imide compounds having a 4-(4-[2-pyrimidinyl]-1-piperazinyl)butyl group attached to the imide nitrogen are useful for alleviating the symptoms of anxiety and depression in human subjects.

16 Claims, No Drawings

CROSS REFERENCE TO RELATED APPLICATION

CROSS REFERENCE TO RELATED APPLICATION

This application is a continuation-in-part of pending application Ser. No. 312,772, filed Jun. 17, 1988 now abandoned claiming priority from PCT International Application No. US86/02224, filed Oct. 21, 1986.

TECHNICAL FIELD

Anxiety and depression are common afflictions which adversely affect a significant portion of the human population. Both anxiety and depression can appear as either acute or chronic disease states, and in certain subjects these disease states can co-exist.

It has been known for many hears that the symptoms of anxiety and depression in human subjects can often be alleviated by the administration of certain chemical substances. In this regard, compounds which are used to treat anxiety are called antianxiety agents, or anxiolytics; while compounds which are used to treat depression are normally termed antidepressants.

In modern medical practiace, a widely-used class of anxiolytics is the benzodiazepines, such as diazepam, and common antidepressants are the so-called "tricyclics," such as imipramine. However, benzodiazepines also have sedative properties in addition to their antianxiety properties. Moreover, tricyclic antidepressants often exhibit undesirable cardiovascular and anticholinergic side-effects.

Accordingly there is a need for new pharmacologic agents for the treatment of anxiety and depression. In particular, there is a need for anxiolytic agents which do not possess sedative effects; i.e., there is a need for anxiolytics which exhibit selectivity of action.

BACKGROUND ART

Certain glutarimide and succinimide compounds, substituted on nitrogen by a (4-aryl-1-piperazinyl)alkyl or (4-heteroaryl-1-piperazinyl)alkyl group, and having tranquillizing, antianxiety and/or anti-emetic properties are known from U.S. Pat. Nos. 3,717,634, 3,907,801, 4,182,763, 4,423,049, 4,507,303, 4,562,255 and 4,543,355. Korgaonka et al., *J. Indian Chem. Soc.*, 60, 874 (1983), disclosed a number of N-(3-[4-aryl-1-piperazinyl]-propyl)camphorimides, which are alleged to have sedative properties in mice.

DISCLOSURE OF INVENTION

This invention relates to new chemical compounds which possess antianxiety and antidepressant properties. More particularly, the compounds of this invention are bridged bicyclic imide compounds of the formula

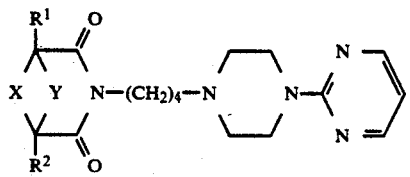

and the pharmaceutically-acceptable acid-addition salts thereof, wherein $R^1$ and $R^2$ are each selected from the group consisting of H and $CH_3$; and either (a) X is selected from the group consisting of $CH_2$, $CH_2CH_2$ and $CH_2CH_2CH_2$; and Y is selected from the group consisting of $CH_2,CH(CH_3)$, $C(CH_3)_2, C(CH_2)_4$ and $CH_2CH_2$;

or (b) X is selected from the group consisting of $CH=CH$, $CH_2CH(CH_3)$ and $CH_2C(CH_3)_2$; and Y is $CH_2$.

Accordingly, this invention provides: (i) the novel compounds of the formula I and the pharmaceutically-acceptable acid-addition salts thereof; (ii) a method of alleviating the symptoms of anxiety in a human subject which comprises administering to said subject a compound of formula I or a pharmaceutically-acceptable acid-addition salt thereof; (iii) a method of alleviating the symptoms of depression in a human subject which comprises administering to said subject a compound of formula I or a pharmaceutically-acceptable acid-addition salt thereof; and (iv) pharmaceutical compositions which comprise a pharmaceutically-acceptable carrier and a compound of formula I or a pharmaceutically-acceptable acid-addition salt thereof.

A preferred group of compounds of the formula I comprises those compounds wherein X is $CH_2CH_2$. Particularly preferred compounds within this preferred group are those wherein $R^1$ is methyl, $R^2$ is hydrogen and Y is $C(CH_3)_2$. An especially preferred individual compound of this invention is the dextrorotatory isomer of 3-(4-[4-(2-pyrimidinyl)-1-piperazinyl]butyl)-1,8, 8-trimethyl-3-azabicyclo[3.2.1]octan-2,4-dione.

DETAILED DESCRIPTION

The compounds of this invention are the compounds of the formula I and salts thereof. In one method according to the invention, the compounds of the formula I are prepared by reaction of a cyclic anhydride of the formula II with the requisite amine of the formula III.

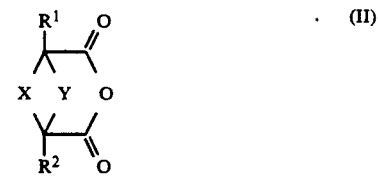

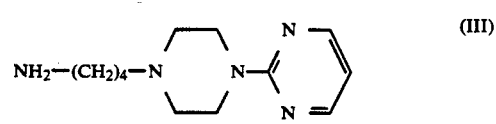

wherein $R^1$, $R^2$, X and Y are as defined previously. The reaction between the anhydride II and the amine III is commonly carried out by heating substantially equimolar quantities of the two compounds at a temperature from 90° to 160° C., until the reaction is substantially complete. The two reactants are usually heated in a reaction-inert solvent; however, in those cases in which one or both of the reactants is molten at the reaction temperature, the two reactants can be heated in the absence of solvent. A reaction-inert solvent is one in which at least one of the reactants is soluble, and which does not adversely interact with either of the starting reactants or the product of the formula I. Typical reaction-inert solvents which can be used include hydrocarbons, such as benzene, toluene, xylene and decalin, and the methyl and ethyl ethers of ethylene glycol, propylene glycol and diethylene glycol. Reaction between an anhydride of the formula II and an amine of the formula III is normally carried out under substantially anhydrous conditions.

Reaction between an anhydride of formula II and an amine of the formula III proceeds more rapidly at high temperatures than lower temperatures, and it proceeds more rapidly in the absence of solvent than when carried out in solution. Thus, in a typical case, reaction of a compound of formula II with a compound of formula III in a reaction-inert solvent at about 120° C. commonly takes several hours, e.g., 12 to 30 hours. However, reaction times of as little as about one hour are sufficient if reaction temperatures of about 220°–30° C. are used.

If no solvent has been used, the compound of formula I is obtained directly. When a reaction-inert solvent has been used, the compound of formula I is usually recovered by solvent evaporation. A compound of formula I can be purified by standard procedures, such as recrystallization and/or chromatography.

The anhydrides of the formula II are normally prepared by dehydration of the corresponding dicarboxylic acid of the formula IV:

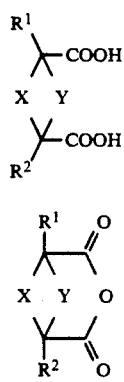

wherein $R^1$, $R^2$, X and Y are as defined previously. This dehydration is carried out under standard conditions, well-known for this kind of transformation. For example, in a typical procedure, a dicarboxylic acid of the formula IV is heated under reflux for a few hours, e.g., two to four hours, in a large excess of acetic anhydride. Removal of the volatile materials by evaporation in vacuo then affords the anhydride of formula II.

The dicarboxylic acids of the formula IV are either known compounds, which are prepared by the known procedures, or they are analogs of known compounds, which are prepared by methods analogous to the known procedures. Methods which are available for preparing dicarboxylic acids of the formula IV include ozonolysis of an olefin of the formula V, nitric acid oxidation of a ketone of the formula VI and permanganate or periodate oxidation of a diketone of the formula VII. Each of these reactions is carried out by methods well-known in the art.

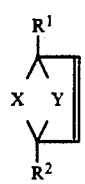

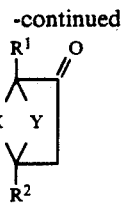

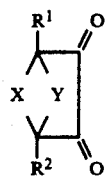

For examples of preparations of specific dicarboxylic acids of the formula IV (or lower-alkyl esters thereof, which can be converted into the acids by conventional hydrolysis methods), consult: *Journal of Organic Chemistry*, 31, 3438 (1969); *Helvetica Chimica Acta*, 53, 2156 (1970); *Journal of the American Chemical Society*, 98, 1810 (1976); *Journal of Organic Chemistry*, 44, 1923 (1979); *Australian Journal of Chemistry*, 34, 665 (1981); and *Canadian Journal of Chemistry*, 59, 2848 (1981).

The amines of the formula III are prepared by known methods. Consult: U.S. Pat. No. 4,423,049.

The compounds of the formula I are basic, and they will form acid-addition salts. All such salts are within the scope of this invention, although for administration to a human subject it is necessary to use a pharmaceutically-acceptable salt. The compounds of formula I contain more than one basic center; consequently, acid-addition salts can incorporate one or more molecules of a salt-forming acid. When more than one molecule of salt-forming acid is incorporated, the anionic counter ions can be the same or different. Acid-addition salts of a compound of the formula I are prepared by conventional methods. In a typical procedure, a compound of formula I is combined with a stoichiometric amount of an appropriate acid in an inert solvent, which can be aqueous, partially aqueous or non-aqueous. The salt is then recovered by solvent evaporation, by filtration if the salt precipitates spontaneously, or by precipitation using a non-solvent followed by filtration. Typical salts which can be prepared include sulfate, hydrochloride, hydrobromide, nitrate, phosphate, citrate, tartrate, pamoate, sulfosalicylate, methanesulfonate, benzenesulfonate and 4-toluenesulfonate salts.

As indicated hereinbefore, the compounds of formula I, wherein $R^1$, $R^2$, X and Y are as defined previously, and the pharmaceutically-acceptable acid-addition salts thereof, are active as antianxiety (anxiolytic) agents. This activity can be demonstrated and measured using the well-known Vogel anti-conflict test. See further, Vogel et al., *Psychophamacologia*, 21, 1 (1971). In a typical variation of the Vogel anti-conflict test, groups of rats are deprived of water for 48 hours, and then they are presented with an opportunity to drink water from an electrified spout. The number of times that the rats drink water (and therefore also receive an electric shock) during a 10 minute period is measured for rats which have been dosed with a test compound (treated rats). This number is compared with the number obtained for control rats, i.e., rats which have not received the test compound. An increase in the number of times that treated rats drink water, over the number of times that control rats drink water, is indicative of antianxiety activity in the compound being tested.

The antianxiety activity of the compounds of the formula I, and the pharmaceutically-acceptable acid-addition salts thereof, makes them useful for administration to humans for alleviating the symptoms of anxiety.

The compounds of the formula I, and the pharmaceutically-acceptable acid-addition salts thereof, have antidepressant properties. Antidepressant activity can be measured in rats using well-known procedures. See further, Porsolt et al., *European Journal of Phamacology*, 47, 379 (1978).

The antidepressant activity of the compounds of the formula I and the pharmaceutically-acceptable acid-addition salts thereof, makes them useful for administration to humans for alleviating the symptoms of depression.

A compound of formula I, or a pharmaceutically-acceptable salt thereof, can be administered to a human subject either alone, or, preferably, in combination with pharmaceutically-acceptable carriers or diluents, in a pharmaceutical composition, according to standard pharmaceutical practice. A compound can be administered orally or parenterally, which includes intravenous and intramuscular administration. However, the preferred route of administration is oral. Additionally, in a pharmaceutical composition comprising a compound of formula I, or a pharmaceutically-acceptable salt thereof, the weight ratio of carrier to active ingredient will normally be in the range from 20:1 to 1:1, and preferably 10:1 to 1:1. However, in any given case, the ratio chosen will depend on such factors as the solubility of the active component, the dosage contemplated, and the precise dosage regimen.

For oral use of a compound of this invention, the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When a compound of the present invention is to be used in a human subject, the daily dosage will be determined by the prescribing physician. In general, the dosage will depend on the age, weight and response of the individual patient, as well as the severity of the patient's symptoms. However, in most instances, an effective anxiety-alleviating amount and an effective depression-alleviating amount of a compound of the formula I, or a pharmaceutically-acceptable acid-addition salt thereof, will be from 1 to 300 mg per-day, and preferably 5 to 100 mg per day, in single or divided doses. Naturally, the more active compounds of the invention will be used at the lower doses, while the less active compounds will be used at the higher doses. Also, for a given compound, an effective depression-alleviating amount will usually be greater than an effective anxiety-alleviating amount.

The following examples and preparations are being provided solely for further illustration. For nuclear magnetic resonance spectra (NMR spectra), absorptions are given in parts per million (ppm) downfield from tetramethylsilane.

EXAMPLE 1

Dextrorotatory Isomer of 3-(4-[4-(2-Pyrimidinyl)-1-piperazinyl]butyl)-1,8,8-trimethyl-3-azabicyclo[3.2.1]octan-2,4-diode A solution of 1.79 g (7.6 mmol) of 1-(4-aminobutyl)-4-(2-pyrimidinyl)piperazine and 1.37 g (7.5 mmol) of d-camphoric anhydride in 50 ml of xylene was heated under reflux for 22 hours with continuous removal of water (Dean-Stark trap). The resulting solution was cooled and evaporated, and the residue was dissolved in 25 ml of warm isopropanol. The solution was allowed to cool, and the solid which appeared was recovered by filtration. This afforded 740 mg (25% yield) of the title compound, mp 94°-95° C., $[alpha]^{20}_D = +7.1°$ (c=10; $C_2H_5OH$)

The $^1$H-NMR spectrum of the product (250 MHz; $CDCl_3$) showed absorptions at 8.24 (d,2H,J=4Hz), 6.41 (t,1H,J=4Hz), 3.76 (t,4H,J=4Hz), 3.63 (m,2H), 2.63 (d,1H), 2.40 (t,4H,J=4Hz), 2.31 (m,2H), 2.20-2.04 (m,2H), 1.94-1.74 (m,2H), 1.74-1.6 (m,2H), 1.54-1.3 (m,4H), 1.1 (s,3H) and 0.87 (m,6H) ppm.

The $^{13}$C-NMR spectrum (250 MHz; $CDCl_3$) showed absorptions at 178.2, 176.2, 161.7, 157.6, 109.7, 58.3, 56.6, 54.4, 53.0, 44.1, 43.7, 39.1, 34.2, 25.7, 25.0, 24.3, 22.0, 19.3 and 14.1 ppm.

The high resolution mass spectrum showed a molecular ion at $M^+ = 399.2616$. $C_{22}H_{33}N_5O_2$: requires $M^+ = 399.2637$.

Analysis: Calcd. for $C_{22}H_{33}N_5O_2$: C,66.12; H,8.34; N,17.53%. Found: C,65.91; H,8.47; N,17.47%.

EXAMPLE 2

Levorotatory Isomer of 3-(4-[4-(2-Pyrimidinyl)-1-piperazinyl]butyl)-1,8,8-trimethyl-3-azabicyclo[3.2.1]octan-2,4-dione Following substantially the procedure of Example 1, 1.27 g (5.39 mmol) of 1-(4-aminobutyl)-4-(2-pyrimidinyl)piperazine was reacted with 0.98 g (5.37 l-camphoric anhydride. The product was chromatographed on silica gel, eluting with dichloromethane/methanol (95:5), to give 0.88 g (42% yield) of the title compound. After recrystallization from isopropanol/hexane, the product had mp 92°-94° C., $[alpha]^{20}_D = 7.4°$ (c=10, $C_2H_5OH$).

The $^1$H-NMR and $^{13}$C-NMR spectra of the product were essentially identical to those of the product of Example 1.

EXAMPLE 3

Racemic 3-(4-[4-(2-Pyrimidinyl)-1-piperazinyl]butyl)-1,8,8-trimethyl-3-azabicyclo[3.2.1]octan-2,4-dione The title compound was prepared from 2.47 g (10.4 mmol) of 1-(4-aminobutyl)-4-(2-pyrimidinyl)piperazine and 1.89 g (10.3 mmol) of dl-camphoric anhydride, substantially according to the procedure of Example 1. This afforded 0.7 g of product, mp 94°-97° C. (17% yield).

The $^1$H-NMR and $^{13}$C-NMR spectra of the product were essentially identical to those of the product of Example 1.

The high resolution mass spectrum showed a molecular ion at M$^+$=399.2669. $C_{22}H_{33}N_5O_2$ requires M$^+$=399.2637.

EXAMPLE 4

3-(4-[4-(2-Pyrimidinyl)-1-piperazinyl]butyl)-3-azabicyclo[3.2.1]octan-2,4-dione

The title compound was prepared from 1.92 g (8.2 mmol) of 1-(4-aminobutyl)-4-(2-pyrimidinyl)piperazine and 1.14 g (8.14 mmol) of 3-oxabicyclo[3.2.1]octan-2,4-dione, substantially following the procedure of Example 1. Yield: 1.0 g (34% yield).

The $^1$H-NMR spectrum of the product (300 MHz; CDCl$_3$) showed absorptions at 8.02 (d,2H,J=4Hz), 6.20 (t,1H,J=4Hz), 3.56 (t,4H,J=4Hz), 3.40 (m,2H), 2.88 (m,2H), 2.22 (t,4H,J=4Hz), 2.12 (m,2H),1.96-1.74 (m,3H), 1.72-1.56 (m,2H), 1.48-1.3 (m,1H) and 1.3-1.1 (m,4H) ppm.

The $^{13}$C-NMR spectrum of the product (300 MHz; CDCl$_3$) showed absorptions at 176.2, 161.4, 157.5, 109.6, 58.0, 52.8, 44.6, 43.4, 38.3, 32.3, 27.0, 25.7 and 23.8 ppm.

The high resolution mass spectrum showed a molecular ion at M$^+$=357.2181. $C_{19}H_{27}N_5O_2$ requires M$^+$=357.2167.

EXAMPLE 5

3-(4-[4-(2-Pyrimidinyl)-1-piperazinyl]-butyl)-3-azabicyclo[3.3.1]nonan-2,4-dione Following substantially the procedure of Example 1, 2.78 g (11.8 mmol) of 1-(4-aminobutyl)-4-(2-pyrimidinyl) piperazine was reacted with 1.88 g (12.2 mmol) of 3-oxabicyclo[3.3.1]nonan-2,4-dione. The product was chromatographed on silica gel, eluting with dichloromethane/methanol (90:10), to give 2.04 g (47% yield) of the title compound.

The $^1$H-NMR spectrum of the product (250 MHz; CDCl$_3$) showed absorptions at 8.25 (d,2H,J=4Hz), 6.42 (t,1H,J=4Hz), 3.88-3.68 (m,6H), 2.86-2.76 (m,2H), 2.45 (t,4H,J=4Hz), 2.37 (m,2H), 2.2-2.07 (m,1H), 2.05-1.88 (m,2H) and 1.74-1.1 (9H,m) ppm.

The $^{13}$C-NMR spectrum of the product (250 MHz; CDCl$_3$) showed absorption at 175.5, 161.7, 157.7, 109.8, 58.3, 53.0, 43.5, 39.3, 38.5, 28.3, 26.2, 24.2 and 19.5 ppm.

The high resolution mass spectrum showed a molecular ion at M$^+$=371.2293. $C_{20}H_{29}N_5O_2$ requires M$^+$=371.2324.

EXAMPLE 6

3-(4-[4-(2-Pyrimidinyl)-1-piperazinyl]butyl)8, 8-dimethyl-3-azabicyclo[3.2.1]octan-2,4-dione Following substantially the procedure of Example 1, 0.54 g (2.34 mmol) of 1-(4-aminobutyl)-4-(2-pyrimidinyl) piperazine was reacted with 0.36 g (2.14 mmol) of 8,8-dimethyl-3-oxabicyclo[3.2.1]octan-2,4-dione. The product was chromatographed on silica gel, eluting with dichloromethane/methanol (96:4), to give 0.25 g (32% yield) of the title compound.

The $^1$H-NMR spectrum of the product (300 MHz; CDCl$_3$) showed absorptions at 8.12 (d,2H,J=3Hz), 6.30 (t,1H,J=3Hz), 3.66 (t,4H,J=4Hz), 3.51 (m,2H), 2.50 (m,2H), 2.32 (t,4H,J=4Hz), 2.23 (m,2H), 2.16-2.02 (m,2H), 1.74-1.6 (m,2H), 1.37 (m,4H), 0.96 (s,3H) and 0.84 (s,3H) ppm.

The $^{13}$C-NMR spectrum of the product (300 MHz; CDCl$_3$) showed absorptions at 176.4, 157.6, 109.7, 58.2, 54.8, 53.0, 43.5, 42.0, 38.5, 26.4, 25.6, 24.1, 23.8 and 20.9 ppm.

The high resolution mass spectrum showed a molecular ion at M$^+$=385.2427. $C_{21}H_{31}N_5O_2$ requires 385.2480.

EXAMPLE 7

3-(4-[4-(2-Pyrimidinyl)-1-piperazinyl]butyl)-1, 5-dimethyl-3-azabicyclo[3.2.1]octan-2,4-dione Following substantially the procedure of Example 1, 4.2 g (17.8 mmol) of 1-(4-aminobutyl)-4-(2-pyrimidinyl) piperazine was reacted with 2.99 g (17.8 mmol) of 1,5-dimethyl-3-oxabicyclo[3.2.1]octan-2,4-dione. The product was chromatographed on silica gel, eluting with dichloromethane/methanol (96:4), to give 1.4 g (21% yield) of the title compound.

The $^1$H-NMR spectrum of the product (300 MHz; CDCl$_3$) showed absorptions at 8.01 (d,2H,J=4Hz), 6.20 (t,1H,J=4Hz), 3.57 (m,4H), 3.45 (m,2H), 2.22 (m,4H), 2.13 (m,2H), 1.70-1.54 (m,5H), 1.38-1.2 (m,5H) and 1.10 (s,6H) ppm.

The $^{13}$C-NMR spectrum of the product (300 MHz; CDCl$_3$) showed absorptions at 178.1, 161.4, 157.5, 109.6 58.1, 52.8, 49.0, 46.5, 43.4, 39.1, 35.8, 25.7, 23.9 and 20.3 ppm.

The high resolution mass spectrum showed a molecular ion at M$^+$=385.2484. $C_{21}H_{31}N_5O_2$ requires M$^+$=385.2480.

EXAMPLE 8

3-(4-[4-(2-Pyrimidinyl)-1-piperazinyl]butyl)-3-azabicyclo[3.2.2]nonan-2,4-dione

An intimate mixture of 0.5 g (2.14 mmol) of 1-(4-aminobutyl)-4-(2-pyrimidinyl) piperazine and 0.22 g (1.42 mmol) of 3-oxabicyclo[3.2.2]nonan-2,4-dione was heated in an oil bath at 220°-230° C. for 15 minutes. An additional 0.22 g (1.42 mmol) of 3-oxabicyclo[3.2.2]nonan-2,4-dione was added. Heating in an oil bath at 220°-230° C. was continued for 15 minutes and then an additional 0.22 g (1.42 mmol) of 3-oxabicyclo[3.2.2]-nonan-2,4-dione was added. Heating was continued for 30 minutes at 220°-230° C. and then the reaction mixture was cooled. The resulting product was chromatographed on silica gel, eluting with dichloromethane/methanol (96:4 followed by 94:6), to give 46 mg of the title compound (6% yield).

The $^1$H-NMR spectrum of the product (300 MHz; CDCl$_3$) showed absorptions at 8.26 (d,2H,J=4Hz), 6.46 (t,$^1$H,J=4Hz), 3.90 (t,4H,J=3Hz), 3.72 (t,2H,J=4Hz), 3.04 (m,2H), 2.68 (t,4H,J=3 Hz), 2.56 (t,2H,J=4Hz), 1.95-1.7 (m, 8H) and 1.64-1.42 (m,4H) ppm.

The $^{13}$C-NMR spectrum of the product (300 MHz; CDCl$_3$) showed absorptions at 178.9, 161.4, 157.7, 110.2 57.6, 52.2, 43.1, 42.4, 41.5, 25.8, 22.7 and 21.8 ppm.

The high resolution mass spectrum showed a molecular ion at M$^+$=371.2316. $C_{20}H_{29}N_5O_2$ requires M$^+$=371.2323.

EXAMPLE 9

3-(4-[4-(2-Pyrimidinyl)-1-piperazinyl]butyl)-8-methyl-3-azabicyclo [3.2.1]octan-2,4-dione can be prepared from 1-(4-aminobutyl)-4-(2-pyrimidinyl)piperazine and 8-methyl-3-oxabicyclo[3.2.1]octan-2,4-dione, substantially following the procedure of Example 1.

3-(4-[4-(2-Pyrimidinyl)-1-piperazinyl]butyl)-8,8-tetramethylene-3-azabicyclo [3.2.1]octan-2,4-dione can be prepared from 1-(4-aminobutyl)-4-(2-pyrimidinyl)piperazine and 8,8-tetramethylene-3-oxabicyclo[3.2.1]octan-2,4-dione, substantially following the procedure of Example 1.

3-(4-[4-(4-Fluoro-2-pyrimidinyl)-1-piperazinyl]butyl)-1, 8,8-trimethyl-3-azabicyclo[3.2.1]octan-2,4-dione can be prepared from 1-(4-aminobutyl)-4-(4-fluoro-2-pyrimidinyl)piperazine and 1,8,8-trimethyl-3-oxabicyclo[3.2.1]octan-2,4-dione, substantially according the procedure of Example 1.

3-(4-[4-(2-Pyrimidinyl)-1-piperazinyl]butyl)-3-azabicyclo[3.2.1]oct-6-en-2, 4-dione can be prepared from 1-(4-aminobutyl)-4-(2-pyrimidinyl)piperazine and 3-oxabicyclo[3.2.1]oct-6-en-2,4-dione, substantially following the procedure of Example 1.

3-(4-[4-(2-Pyrimidinyl)-1-piperazinyl]butyl)-6-methyl-3-azabicyclo [3.2.1]octan-2,4-dione can be prepared from 1-(4-aminobutyl)-4-(2-pyrimidinyl)piperazine and 6-methyl-3-oxabicyclo[3.2.1]octan-2,4-dione, substantially following the procedure of Example 1.

3-(4-[4-(2-Pyrimidinyl)-1-piperazinyl]butyl)-6,6-dimethyl-3-azabicyclo [3.2.1]octan-2,4-dione can be prepared from 1-(4-aminobutyl)-4-(2-pyrimidinyl)piperazine and 6,6-dimethyl-3-oxabicyclo[3.2.1]octan-2,4-dione, substantially following the procedure of Example 1.

3-(4-[4-(4-Fluoro-2-pyrimidinyl)-1-piperazinyl]butyl)-3-azabicyclo [3.2.1]oct-6en-2,4-dione can be prepared from 1-(4-aminobutyl)-4-(4-fluoro-2-pyrimidinyl)piperazine and 3-oxabicyclo[3.2.1]oct-6-en-2,4-dione, substantially following the procedure of Example 1.

EXAMPLE 10

Mono-hydrochloride Salt of the Dextrorotatory Isomer of 3-(4-[4-(2-Pyrimidinyl)-1-piperazinyl]butyl)-1,8,8-trimethyl-3-azabicyclo [3.2.1]octan-2,4-dione To a refluxing solution of 1.04 g (2.6 mmol) of the dextrorotatory isomer of 3-(4-[4-(2-pyrimidinyl)-1-piperazinyl]butyl)-1, 8,8-trimethyl-3-azabicyclo[3.2.1]-octan-2,4-dione in 5 ml of isopropanol was added 0.55 ml (2.65 mmol) of 4.8N aqueous hydrochloric acid. The resulting solution was allowed to cool to room temperature, and then the volume was reduced to 3 ml by evaporation in vacuo. An additional 5 ml of isopropanol was added and the solution was heated to the boiling point. The solution was allowed to cool slowly, with stirring. The solid which appeared was collected by filtration, to give 0.64 g (56% yield) of the title salt, mp 207°–08° C.

The $^{13}$C-NMR spectrum (250 MHz; D$_2$O) showed absorptions at 182.4, 180.8, 161.3, 159.6, 113.0, 57.3, 55.7, 52.3, 45.4, 42.2, 39.4, 34.8, 25.8, 25.1, 22.04, 22.0, 19.3 and 14.3 ppm.

Analysis: Calcd. for $C_{22}H_{33}N_5O_2 \cdot HCl$: Cl, 8.13%. Found: Cl, 8.02%.

PREPARATION 1

3-Oxabicyclo[3.2.2]nonan-2,4-dione

A solution of 2.9 g of cis-cyclohexane-1,4-dicarboxylic acid in 25 ml of acetic anhydride was heated under reflux for 2.5 hours. The solvent was removed by evaporation in vacuo, and the residue was triturated under diethyl ether several times. The residue was dried under high vacuum to give 2.5 g (97% yield) of the title compound.

The $^{13}$C-NMR spectrum of the product (300 MHz; CDCl$_3$) showed absorptions at 170.5, 41.4 and 25.2 ppm.

The $^1$H-NMR spectrum of the product (300 MHz; CDCl$_3$) showed absorptions at 2.24–1.34 (m,8H) and 2.5 (m,2H) ppm.

PREPARATION 2

3-Oxabicyclo[3.2.1]octan-2,4-dione

A solution of 1.63 g of cis-cyclopentane-1,3-dicarboxylic acid in 8.2 ml of acetic anhydride was heated in an oil bath at ca. 100° C. for 45 minutes. The excess acetic anhydride and acetic acid were removed by evaporation in vacuo to give a solid which was triturated under diethyl ether. This afforded 1.14 g (79% yield) of the title anhydride.

The $^{13}$C-NMR spectrum of the product (300 MHz; CDCl$_3$) showed absorptions at 170.1, 41.8, 31.1 and 26.4 ppm.

The $^1$H-NMR spectrum of the product (300 MHz; CDCl$_3$) showed absorptions at 3.2 (M,2H), 2.36–1.9 (m,8H) and 1.82–1.66 (m,2H) ppm.

PREPARATION 3

1,8,8-Trimethyl-3-oxabicyclo[3.2.1]octan-2,4-dione (1-Camphoric Anhydride)

The product of Preparation 5 was cyclized with acetic anhydride, using the procedure of Preparation 2, to give 1.0 g (97% yield) of the title compound.

PREPARATION 4 cis-Cyclohexane-1,4-dicarboxylic Acid

A steady stream of ozone was passed through a mixture of 15 g (0.14 mole) of bicyclo[2.2.2]oct-2-ene and 300 ml of methanol at −70° C. for 4 hours. The ozone stream was stopped, the mixture was allowed to warm to room temperature, and then the solvent was removed by evaporation in vacuo. The residue was dissolved in 72 ml of formic acid, and to the resulting solution was added, cautiously, portionwise, 50 ml of 30% hydrogen peroxide. The resulting mixture was heated to 70° C., at which point an exothermic reaction took place. After the exothermic reaction had subsided, the reaction mixture was heated under reflux for 1 hour. Concentration of the reaction mixture in vacuo afforded a colorless oil, which was partitioned between 300 ml of ethyl acetate and 300 ml of water. The pH was adjusted to 9.5 using 2N sodium hydroxide. The aqueous phase was removed, acidified to pH 2.0, and extracted with fresh ethyl acetate. The ethyl acetate extract was dried (Na$_2$SO$_4$) and evaporated in vacuo. The residue was recrystallized from water to give 3.0 g (13% yield) of cis-cyclohexane-1,4-dicarboxylic acid.

The $^{13}$C-NMR spectrum of the product (300 MHz; CDCl$_3$) showed absorptions at 177.1, 39.8 and 25.2 ppm.

PREPARATION 5

1,2,2-Trimethyl-cis-cyclopentane-1,3-dicarboxylic Acid (1-Camphoric Acid)

A solution of 1.0 g (7.2 mmol) of 1,7,7-trimethyl-bicyclo[2.2.1]hept-2-ene in 20 ml of methanol was to −75° C., and a steady stream of ozone was passed through the solution for 1 hour. Excess ozone was removed using a stream of nitrogen, and then the reaction mixture was warmed to room temperature and evaporated in vacuo. The residue was dissolved in 10 ml of formic acid, and 5 ml of 30% hydrogen peroxide was added portionwise. The reaction mixture was heated to ca. 75° C., at which point an exothermic reaction took place. After the exothermic reaction had subsided, the resulting mixture was heated under reflux for 1.5 hours. The cooled mixture was evaporated in vacuo to give 1.1 g (78% yield) of the title compound.

PREPARATION 6

1,7,7-Trimethylbicyclo[2.2.1]hept-2-ene 1,7,7-Trimethylbicyclo[2.2.1]heptan-2-one (1-camphor) was converted into its 4-toluenesulfonylhydrazone, which was then reacted with methyllithium in ether, to give the title compound. The method used was that described by Shapiro and Duncan, *Organic Synthesis*, Vol 51, pp 67–69, for the conversion of racemic camphor into racemic 1,7,7-trimethylbicyclo[2.2.1]hept-2-ene.

I claim:

1. A bridged bicyclic imide compound of the formula

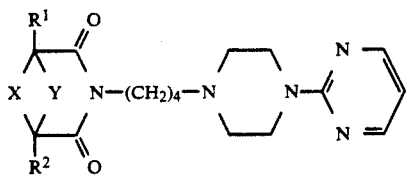

and the pharmaceutically-acceptable acid-addition salts thereof, wherein $R^1$ and $R^2$ are each selected from the group consisting of H and $CH_3$; and either (a) X is selected from the group consisting of $CH_2$, $CH_2CH_2$ and $CH_2CH_2CH_2$; and Y is selected from the group consisting of $CH_2$, $CH(CH_3)$, $C(CH_3)_2$, $C(CH_2)_4$ and $CH_2CH_2$;

or (b) X is selected from the group consisting of $CH=CH$, $CH_2CH(CH_3)$ and $CH_2C(CH_3)_2$; and Y is $CH_2$.

2. A compound according to claim 1 wherein X is selected from the group consisting of $CH_2$, $CH_2CH_2$ and $CH_2CH_2CH$; and Y is selected from the group consisting of $CH_2$, $CH(CH_3)$, $C(CH_3)_2$, $C(CH_2)_4$ and $CH_2CH_2$.

3. A compound according to claim 2 wherein X is $CH_2CH_2$.

4. A compound according to claim 3 wherein $R^1$ and $R^2$ are each H and Y is $CH_2$.

5. A compound according to claim 3 wherein $R^1$ and $R^2$ are each H and Y is $CH_2CH_2$.

6. A compound according to claim 3 wherein $R^1$ is $CH_3$, $R^2$ is H and Y is $C(CH_3)_2$.

7. The dextrorotatory isomer of 3-(4-[4-(2-pyrimidinyl)-1-piperazinyl]butyl)-1,8,8-trimethyl-3-azabicyclo[3.2.1]octan-2,4-dione, a compound according to claim 6.

8. A compound according to claim 1, wherein X is selected from the group consisting of $CH=CH$, $CH_2CH(CH_3)$ and $CH_2C(C_3)_2$; and Y is $CH_2$.

9. A compound according to claim 8 wherein $R^1$ and $R^2$ are each H and X is $CH_2CH(CH_3)$.

10. A method of alleviating the symptoms of anxiety in a human subject, which comprises administering to said subject an effective anxiety-alleviating amount of a bridged bicyclic imide compound according to claim 1.

11. The method according to claim 10, wherein said bridged bicyclic imide compound is 3-(4-[4-(2-pyrimidinyl)-1-piperazinyl]butyl)-3-azabicyclo[3.2.1]octan-2,4-dione.

12. The method according to claim 10, wherein said bridged bicyclic imide compound is the dextrorotatory isomer of 3-(4-[4-(2-pyrimidinyl)-1-piperazinyl]-butyl)-1,8,8-trimethyl-3-azabicyclo[3.2.1]octan-2,4-dione.

13. A method of alleviating the symptoms of depression in a human subject, which comprises administering to said subject an effective depression-alleviating amount of a bridged bicyclic imide compound according to claim 1.

14. The method according to claim 13, wherein said bridged bicyclic imide compound is 3-(4-[4-(2-pyrimidinyl)-1-piperazinyl]butyl)-3-azabicyclo[3.2.1]-octan-2,4-dione.

15. The method according to claim 13, wherein said bridged bicyclic imide compound is the dextrorotatory isomer of 3-(4-[4-(2-pyrimidinyl)-1-piperazinyl]-butyl)-1,8,8-trimethyl-3-azabicyclo[3.2.1-dione.

16. A pharmaceutical composition which comprises a pharmaceutically-acceptable carrier and a bridged bicyclic imide compound according to claim I, wherein the weight ratio of said carrier to said compound according to claim 1 is in the range from 20:1 to 1:1.

* * * * *